(12) United States Patent
Bergeron

(10) Patent No.: US 6,399,662 B1
(45) Date of Patent: Jun. 4, 2002

(54) METHOD AND COMPOSITION FOR THE TREATMENT OF DIARRHEA AND GASTROINTESTINAL SPASMS

(75) Inventor: Raymond J. Bergeron, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/734,660

(22) Filed: Dec. 13, 2000

(51) Int. Cl.$^7$ .............................................. A61K 31/13
(52) U.S. Cl. ...................... 514/579; 514/674; 514/740; 514/861
(58) Field of Search .................................. 514/579, 674, 514/740, 867

(56) References Cited

U.S. PATENT DOCUMENTS

| | | |
|---|---|---|
| 5,393,757 A | 2/1995 | Bergeron, Jr. et al. |
| 5,462,970 A | 10/1995 | Bergeron, Jr. et al. |
| 5,962,533 A | * 10/1999 | Bergeron, Jr. ............... 514/674 |

OTHER PUBLICATIONS

Bergeron, Jr., et al., *J. Med. Chem*, "Metabolically Programmed Polyamine Analogue Antidiarrheals", vol. 39, pp. 2461–2471 (1996).

Bergeron, Jr., et al., "Polyamine Analogue Antidiarrheals: A Structure–Activity Study", *J. Med. Chem.*, Nov. 21, 2000.

Sninsky, C.A.; Marchand, S.D.: Bergeron, R. "Effect of Diethylhomospermine (DEHSPM) on Visceral Motor Response from Rectal Balloon Distension", Gastroenterology 1996, 110, A761.

Sninsky, C.A.; Bergeron, R. "Potent Anti–Diarrheal Activity of a New Class of Compounds: Synthetic Analogues of the Polyamine Pathway", Gastroenterology 1993, 104, A54.

Sninsky, C.A.; Broome TA, Brooderson RJ, Bergeron RJ; "Diethylhomospermine, a synthetic polyamine analog, prevents psychological stress–induced acceleration of colonic transit in rats", Gastroenterology 106:A569, 1994.

* cited by examiner

*Primary Examiner*—Rebecca Cook
(74) *Attorney, Agent, or Firm*—Miles & Stockbridge; Dennis P. Clarke

(57) ABSTRACT

Anti-diarrheal and/or gastrointestinal anti-spasmodic pharmaceutical compositions containing [A] a polyamine of the formula:

$$R_1—N^1(R_2)—(CH_2)x—N^2H—Q—N^3H—(CH_2)y—N^4(R_3)—R_4 \quad (I)$$

wherein: $R_1$, $R_2$, $R_3$ and $R_4$ may be the same or different and are H, alkyl, cycloalkyl or aralkyl having from 1 to 12 carbon atoms, or a heterocyclic group having from 3 to 10 atoms wherein the hetero atom is said $N^1$ or $N^4$;

Q is a cycloalkyl group having from 3 to 10 carbon atoms;

x is an integer from 3 to 6, inclusive;

and y is an integer from 3 to 6, inclusive;

or (II) a salt thereof with a pharmaceutically acceptable acid; and [B] a pharmaceutically acceptable carrier therefor as well as methods of treatment utilizing the polyamines are disclosed.

7 Claims, 1 Drawing Sheet

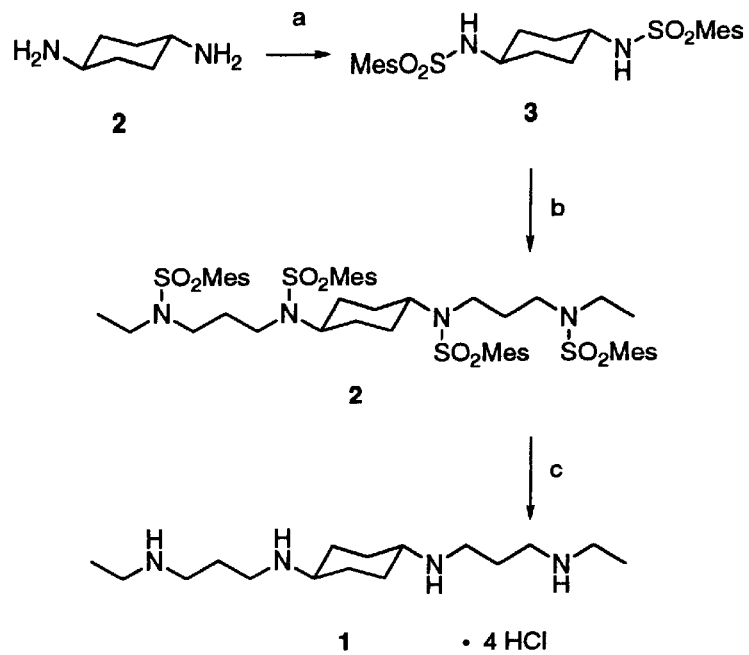
<sup>a</sup> Reagents: (a) Mesitylenesulfonyl chloride, NaOH (aq), CH$_2$Cl$_2$, 82%; (b) NaH, $N$-(3-bromopropyl)-$N$-ethylmesitylenesulfonamide, DMF, 73%; (c) 30% HBr in HOAc, PhOH, CH$_2$Cl$_2$; NaOH; HCl, 64%.
Figure

METHOD AND COMPOSITION FOR THE TREATMENT OF DIARRHEA AND GASTROINTESTINAL SPASMS

This invention was made with United States Government support under Grant NCDDG-CA37606, awarded by the National Cancer Institute. The United States Government has certain rights in this invention.

BACKGROUND OF THE INVENTION

The present invention relates to certain novel anti-diarrheal and gastrointestinal anti-spasmodic agents and methods of treatment and pharmaceutical compositions based thereon.

DESCRIPTION OF THE PRIOR ART

Diarrhea can result from a variety of pathophysiological disorders including bacterial and parasitic infections, disease or debilitation of organs such as liver, adrenal and others. It can also occur as a result of other therapy or diet. In all cases, diarrhea is generally a symptom of organic gastrointestinal disorders and not itself a disorder. Chronic diarrhea is generally due to: (1) hypersecretion of fluid and electrolytes of the stomach, small intestine and colon; (2) inability to absorb certain nutrients (malabsorption); and (3) intestinal hypermotility and rapid transport. These may occur separately or in combination. Certain disorders may have diarrhea as a prominent feature of the disease/syndrome, but the specific etiology is unclear. In this latter group, emotional tension and psychological factors may adversely influence the frequency of the symptoms.

Diarrhea and diarrheal diseases are one of the most frequent causes of morbidity and mortality, especially in less developed countries wherein the number of those killed by such diseases is estimated at about 5 million persons per annum. Particularly dangerous are diarrheal diseases of the newborn and the youngest group of babies (S. Hughes: Drugs, Vol. 26, pp. 80–90 (1983)).

In mechanized or automated large capacity farms, diarrhea and infections of the gastrointestinal tract are frequent, especially with young livestock and the high mortality or growth deceleration thereof have a considerable negative economical effect. Diarrheal diseases of man and animals are caused by a plurality of etiological factors, especially of microbial and viral character. The most prevalent microbes are gram-negative bacteria, *Escherichia coli* and *Vibrio cholerae*. However, it is now clear that other bacteria, viruses and parasites (protozoan, amoeba, etc.) also cause severe problems.

Diarrheal diseases are treated by rehydration therapy using preparations composed of various salts (potassium chloride, sodium chloride, sodium hydrogen carbonate) and glucose, whereby quick compensation for the loss of water and ions, as well as for acidosis, occurs. However, the occurrence of diarrheal diseases is not influenced. Other substances of the same kind produce similar results.

Anti-diarrheal compounds are, of course, well known in the medicinal arts and take various forms. In particular, there are a variety of products known which act systemically to provide anti-diarrheal effects when administered in a manner which will enable the drug to be taken into the system at effective therapeutic levels.

In addition, there are anti-cholinergic substances applied together with spasmolytics such as Reasec. RTM. (Janssen) which contain diphenyloxylate and atropin. Both human and veterinary medicine use chemotherapeutic agents with anti-bacterial effects, such as sulfonamides, or antibiotics are availed of which are apt to suppress certain infections.

Medicaments are also aimed at the sphere of regulation depending on receptors, especially those localized on the basolateral membrane, further by means of an intracellular mechanism of intervention by the so-called secondary messenger, and by influencing the transport mechanism, especially boundary membranes. The modulation of receptor-dependent regulation mechanisms can be influenced, to some extent, by medicaments of the type alpha.sub.2 adrenergic agonists such as clonidine (Catapresan.RTM.) (E. B. Chang et al, Gastroenterology, Vol. 91, pp. 564–569 (1986)), somatostatin, or encephalin and morphine analogs. For influencing the transport of ions through the membrane, it is also possible to use alpha.sub.2 adrenergic agonists (E. B. Chang et al, Am. J. Physiol., Vol. 1982, p. 242). Reference has also been made to the use of lidamidine, i.e., the medicament having a damping effect on the intestine peristaltics (M. D. Dharmsathphom: Gastroenterology, Vol. 91, pp. 769–775 (1986)).

Disadvantages of anti-diarrheal medicaments, i.e., those referred to in professional papers rather than those medicaments of this type applied in practice, include their secondary strong effects such as antihypertensive effects (clonidine), growth factors (somatostatin), habituation and/or incomplete preclinical research (encephalin derivatives). The application of large doses of antibiotics and long administration thereof has not proved optimum in epidemical diarrhea localities. Where the diarrhea-inducing agent is cholera toxin, however, there does not exist any efficient protection, exception for inoculum which is not sufficiently potent either, and gives short-term protection only (3 months) and low efficiency (30–40%).

In recent years, a great deal of attention has been focused on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta., Vol. 473, p. 241 (1978); Fillingame et al, Proc. Natl. Acad. Sci. U.S.A., Vol. 72, p. 4042 (1975); Metcalf et al, J. Am. Chem. Soc., Vol. 100, p. 2551 (1978); Flink et al, Nature (London), Vol. 253, p. 62 (1975); and Pegg et al, Polyamine Metabolism and Function, Am. J. Cell. Physiol., Vol. 243, pp. 212–221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, Science, Vol. 149, p. 48 (1965); Russell et al, Polyamines as Biochemical Markers of Normal and Malignant Growth (Raven, New York, 1978); Hirschfield et al, J. Bacteriol., Vol. 101, p. 725, (1970); Hafner et al, J. Biol. Chem., Vol. 254, p. 12419 (1979); Cohn et al, J. Bacteriol., Vol. 134, p. 208 (1978); Pohjatipelto et al, Nature (London), Vol. 293, p. 475 (1981); Mamont et al, Biochem. Biophys. Res. Commun., Vol. 81, p. 58 (1978); Bloomfield et al, Polyamines in Biology and Medicine (D. R. Morris and L. J. Morton, eds., Dekker, New York, 1981), pp. 183–205; Gosule et al, Nature, Vol. 259, p. 333 (1976); Gabbay et al, Ann. N. Y. Acad. Sci., Vol. 171, p. 810 (1970); Suwalsky et al, J. Mol. Biol., Vol. 42, p. 363 (1969); and Liquori et al, J. Mol. Biol., Vol. 24, p. 113 (1968).

However, regardless of the reason for increased polyamine levels, the phenomenon can be and has been exploited in chemotherapy. See Sjoerdsma et al, Butterworths Int. Med. Rev.: Clin. Pharmacol. Thera., Vol. 35, p. 287 (1984); Israel et al, J. Med. Chem., Vol. 16, p. 1 (1973); Morris et al, Polyamines in Biology and Medicine; Dekker, New York, p. 223 (1981); and Wang et al, Biochem. Biophys. Res. Commun., Vol. 94, p. 85 (1980).

It has been previously reported that diethylhomospermine (DEHSPM) inhibited myoelectric activity and transit of the small intestine in rats [J. Gastro. Motil., Vol. 1, p. 53 (1989)]. This inhibition was reversed with co-administration of bethanechol, a cholinergic agonist, but not with other agonists or antagonists [Gastro., Vol. 98, p. A388 (1990)]. However, there is no suggestion or disclosure in the prior art that any of the above-described polyamines have utility as anti-diarrheal or gastrointestinal anti-spasmodic agents.

Recently, it has been found that certain polyamines function effectively as anti-diarrheal and gastrointestinal antispasmodic agents. See U.S. Pat. Nos. 5,393,757 and 5,462,970, the entire contents and disclosures of which are incorporated herein by reference. See also Bergeron et al, J. Med. Chem, Vol. 39, pp 2461–2471 (1996); which discloses that certain hydroxy-substituted polyamines are effective anti-diarrheal agents.

In a series of studies, Tansy was able to demonstrate that polyamines have a profound impact on the motility of the gastrointestinal (UI) tract. The original work focused on poly(ethylenimine) and gastric emptying in rodents and dogs. Branched-chain poly(ethylenimine)s effected significant inhibition of gastric emptying in rodents; however, they caused a severe retch response in dogs. Because of the structural relationship between the poly(ethylenimine)s and natural polyamines, Tansy elected to evaluate the effect of spermidine, spermine, and a group of polyamine analogues on the gastric emptying of rodents. It soon became clear that polyamines had a substantial influence on gastric emptying and that "endogenous spermine and spermidine may have some unrecognized GI secretomotor activity". [See Spermine and Spermidine as Inhibitors of Gastrointestinal Motor Activity, Surg. Gyn. Obst, 1982, 154, 74–80; Pharmacology of Polyethylenimine I:Effects on Gastric Emptying In Rats, J. Pharm. Sci. 1977, 66. 899–901; GI Pharmacology of Polyethylenimine II: Motor Activity in Anesthesthetized Dogs, J. Pharm Sci. 1977, 66,902–904; Effects of Spermine and Spermidine on Gastric Emptying in Rats, J. Pharm. Sci 1981, 70 347]. From a structure-activity perspective, it also became obvious that minor changes in the polyarnine's structure could completely eradicate the molecule's ability to inhibit gastric emptying. These studies strongly suggested that the polyarnine pharmacophore was an excellent candidate for the construction of antitransit, antidiarrheal drugs.

One polyamine analogue designed and synthesized by the present inventor, $N^1$, $N^{14}$ diethylhomospermine (DEHSPM), is a very potent antidiarrheal. This has been demonstrated in a number of animal models and, in the clinic against AIDS-related diarrhea. However, DEHDSPM is N-deethylated to homospermine (HSPM), which has a very protracted half life: 2–3 weeks in mice and even longer in the dog. Each succeeding dose of DEHSPM results in a further accumulation of HSPM until toxic levels of the latter tetraamine are reached, a troublesome metabolic property in animals. [See Structural Specificity of Synthetic Analogues of Polyamines and their Effect on Gastrointestinal Motility, *Polyamines and the Gastrointetinal Tract*, Falk Symposium, NO. 62; Kluwer Academic: Boston, 1991; Potent Anti-Diarrheal Activity of a New Class of Compounds: Synthetic Analogues of the Polyamine Pathway. *Gastroenterology* 1993, 104, A54; J. Metabolism and Pharmacokinetics of $N^1$, $N^{14}$-Diethylhomospermine. Drug Metab. Dispos. 1996, 24, 334–843].

It is an object of the present invention to provide novel anti-diarrheal and gastrointestinal antispasmodic pharmaceutical, compositions and methods of treatment based upon certain polyamines other than those described in the prior art as effective therefor.

BRIEF DESCRIPTION OF THE DRAWINGS

The FIGURE is a reaction scheme for preparing the polyamines employed in the practice of the invention.
Synthesis of CHX(3,4,3)-trans
N,N'-Bis[3-(ethylamino)propyl]-trans-1,4-cyclohexanediamine tetrahydrochloride [CHX(3,4,3)-trans, 1] was assembled via fragment synthesis (Scheme 1). Disulfonamide 3, available in 90% yield from reaction of trans-1,4-diaminocyclohexane (2) with mesitylenesulfonyl chloride (2 equiv) under biphasic conditions, was alkylated with N-(3-bromopropyl)-N-ethylmesitylenesulfonamide (2 equiv, NaH, DMF) to provide protected polyamine 4 in 73% yield. The amino groups of 4 were unmasked with 30% HBr in acetic acid and phenol, furnishing final product 1 in 64% yield. [Bergeron et al, J. Med. Chem., Vol. 7, pp3464–3476 (1984)]

SUMMARY OF THE INVENTION

The foregoing and other objects are realized by the present invention, one embodiment of which is an anti-diarrheal, anti-secretory, or gastrointestinal anti-spasmodic pharmaceutical composition comprising an anti-diarrheal or gastrointestinal antispasmodic (hereinafter "GI antispasmodic") effective amount of a compound of the formula set forth below and a pharmaceutically acceptable carrier therefor.

An additional embodiment of the present invention comprises a method of treating a human or nonhuman animal in need thereof comprising administering to the animal an anti-diarrheal or GI antispasmodic effective amount of a compound of the formulae below.

Suitable methods for the preparation of polyamines for use in the composition and method of the invention are those described in application Ser. No. 07/210,520 filed Jun. 23, 1988, now U.S. Pat. No. 5,091,576, the entire contents and disclosure of which is incorporated herein by reference.

The polyamines suitable in the practice of the invention include those having the formula:

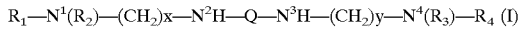

wherein: $R_1$, $R_2$, $R_3$ and $R_4$ may be the same or different and are H, alkyl, cycloalkyl or aralkyl having from 1 to 12 carbon atoms, or a heterocyclic group having from 3 to 10 atoms wherein the hetero atom is said $N^1$ or $N^4$;

Q is a cycloalkyl group having from 3 to 10 carbon atoms;
x is an integer from 3 to 6, inclusive;
and y is an integer from 3 to 6, inclusive;
or (II) a salt thereof with a pharmaceutically acceptable acid.

DETAILED DESCRIPTION OF THE INVENTION

The present invention is predicated on the discovery that polyamines of the above formula act to inhibit the potential for the large and small intestines to contract. While not wishing to be bound by any theory as to the mechanism of action of the polyamines as inhibitors of this action of the intestines, it is hypothesized that the polyamines function via a receptor-dependent regulation mechanism whereby the myoelectric activity of the muscle tissue of the colon and small intestine and the secretion of fluid and electrolytes by these organs are modulated. In addition, some of these above effects may be directly or indirectly mediated through the release of nitric oxide or through the activation of nitric oxide synthase.

For each of the utilities mentioned herein, the amount required of active agent, the frequency and mode of its administration will vary with the identity of the agent concerned and with the nature and severity of the condition being treated and is, of course, ultimately at the discretion of the responsible physician or veterinarian. In general, however, a suitable dose of agent will lie in the range of about 0.0001 mg to about 500 mg per kilogram of mammal body weight being treated. Administration by the parenteral route (intravenously, intradermally, intraperitoneally, intramuscularly or subcutaneously) is preferred for a period of time of from one to ten days; although the agent may also be administered orally. For chronic problems, the drug is administered as needed, subcutaneously, intravenously, or orally.

While it is possible for the agents to be administered as the raw substances, it is preferable, in view of their potency, to present them as a pharmaceutical formulation. The formulations of the present invention, both for veterinary and human use, comprise the agent together with one or more acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

The pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. The dosage of the active substance depends on the species of warm-blooded animal and on the age and individual condition the illness to be treated and also on the mode of administration.

The novel pharmaceutical preparations contain from approximately 10% to approximately 95%, and preferably from approximately 20% to approximately 90%, of the active substance. Pharmaceutical compositions according to the invention can, for example, be in unit dose form, such as drages, tablets, capsules, suppositories or ampoules, and contain from approximately 0.05 g to approximately 10.0 g, and preferably from approximately 0.3 g to approximately 1.0 g, of the active ingredient.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragee cores. In so doing, they can also be incorporated into plastic carriers which release the active substances or allow them to diffuse in controlled amounts.

Suitable carriers are especially fillers such as guars, for example, lactose, saccharose, mannitol or sorbitol, cellulose preparations and/or calcium phosphates, for example, tricalcium phosphate or calcium hydrogen phosphate, also potato starch, gelatin, tragacanth, methylcellulose, hydroxypropylmethylcellulose, sodium carboxymethy 1 cellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially useful, such as flow-regulating and lubricating agents, for example, silica, talc, stearic acid or salts thereof such as magnesium or calcium stearate, and/or polyethylene glycol. Dragee cores are provided with suitable coatings that are, if desired, resistant to gastric juice, there being used, inter alia, concentrated sugar solutions which optionally contain gum arabic, talc, polyvinylpyrrolidone, polyethylene-glycol and/or titanium dioxide, lacquer solutions in suitable organic solvents or solvent mixtures or for the manufacture of coatings that are resistant to gastric juice, solutions of suitable cellulose, preparations such as acetylcellulose phthalate or hydroxypropylmethylcellulose phthalate. Coloring substances or pigments can be added to the tablets or coatings, for example for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally, stabilizers. In soft capsules, the active ingredient is preferably dissolved or suspended in suitable liquids or wax-like substances such as fatty oils, paraffin oil or polyethylene glycols, it being possible also for stabilizers to be added. Other forms of oral administration are, for example, syrups prepared in a customary manner that contain the active ingredient in, for example, suspended form and in a concentration of approximately from 5% to 20%, and preferably approximately 10%, or in a similar concentration that provides a suitable single dose when administered, for example, in measures of 5 or 10 ml. Also suitable are, for example, powdered or liquid concentrates for preparing shakes, for example, in milk. Such concentrates can also be packed in single-dose quantities.

Particularly suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

Such formulations may optionally contain one or more additional ingredients among which may be mentioned preservatives, such as methyl hydroxybenzoate, chlorocresol, metacresol, phenol and benzalkoniurn chloride. Such materials are of special value when the formulations are presented in multi-dose containers.

Buffers may also be included to provide a suitable pH value for the formulation and suitable materials include sodium phosphate and acetate. Sodium chloride or glycerin may be used to render a formulation isotonic with the blood. If desired, the formulation may be filled into the containers under an inert atmosphere such as nitrogen or may contain an anti-oxidant and are conveniently presented in unit dose or multi-dose form, for example, in a sealed ampoule.

It will be appreciated that while the agents described herein form acid addition salts and carboxyl acid salts, the biological activity thereof will reside in the agent itself. These salts may be used in human and in veterinary medicine and presented as pharmaceutical formulations in the manner and in the amounts (calculated as the base) described herein above, and it is then preferable that the acid moiety be pharmacologically and pharmaceutically acceptable to the recipient. Examples of such suitable acids include (a) mineral acids: hydrochloric, hydrobromic, phosphoric, metaphosphoric, and sulfuric acids; (b) organic acids: tartaric, acetic, citric, malic, lactic, fumaric, benzoic, glycollic, gluconic, gulonic, succinic and arylsulfonic, for example, p-toluenesulfonic acids.

In compounds of the invention, R1 and R2 are preferably methyl, ethyl, propyl, benzyl, etc., it being understood that the term "aralkyl" is intended to embrace any aromatic group, the chemical and physical properties of which do not adversely affect the efficacy and safety of the compound for therapeutic applications. Preferred, however, are the hydrocarbyl aralkyl groups, i.e., comprised only of C and H atoms.

Polyamines of the above formula are synthesized according to the methods described in application Ser. No. 07/210, 520 filed Jun. 23, 1988, now U.S. Pat. No. 5,091,576, and Ser. No. 07/870,441 filed Oct. 9, 1991, the entire contents and disclosures of both of which are incorporated herein by reference.

The invention is illustrated by the following non-limiting examples.

EXAMPLE 1

Synthesis of CHX(3,4,3)-trans

Referring to FIG. 1, N,N'-Bis[3-(ethylamino)propyl]-trans-1,4-cyclohexanediamine tetrahydrochloride [CHX(3,4,3)-trans, 1] was assembled via a fragment synthesis (Scheme 1) Disulfonamide 3, available in 90% yield from reaction of trans-1,4-diaminocyclohexane (2) with mesitylenesulfonyl chloride (2 equiv) under biphasic conditions, was alkylated with N-(3bromopropyl)-N-ethylmesitylenesulfonamide (2 equiv, NaH, DMF) to provide protected polyamine 4 in 73% yield. The amino groups of 4 were unmasked with 30% HBr in acetic acid and phenol, furnishing the final product 1 in 64% yield.

EXAMPLE 2

Castor Oil-Induced Diarrhea in Rats

Male Sprague-Dawley rats (350–400 g, Harlan Sprague-Dawley, Indianapolis, Ind.) were fasted overnight in hanging wire cages and allowed free access to water. A typical experiment involved 20 rats: 5 untreated controls and 5 pretreated with polyamine analogues at each of three doses (typically equivalent on a molar basis to 1, 5, 10, or 25 mg/kg of DEHSPM) as either a sc injection or a po gavage 30 min prior to castor oil. All animals were then challenged with castor oil (purchased from a local drugstore) as a gastric gavage of 5 mL/kg of body weight at t=0 and monitored for the onset and duration of diarrhea at 30-min intervals for a 6-h period during which they received no food or water (Eaker, E. Y.; Bixler, G. B.; Mathias, J. R., J. Pharm Exp. Ther. 1988, 246, 786–789). Onset of diarrhea for the control rats was between 30 and 90 min and lasted for at least 6 h. The animal weight and stool weight were recorded at 2, 4, and 6 h.

EXAMPLE 3

Irritable Bowel Syndrome in Rats

Male Sprague-Dawley rats (200–350 g, Harlan Sprague-Dawley, Indianapolis, Ind.) were housed in hanging wire cages in a temperature- and humidity-controlled room with a 12hour light/dark cycle; the animals were fasted overnight (unless non-fasted rats were utilized in experiments involving PO administration) and allowed free access to water. Animal care and experimental procedures were approved by the Institutional Animal Care and Use Committee. A typical experiment involved 20 rats: 5 untreated controls and 5 pretreated with polyamine analogues at each of three doses as either a SC injection or a PO gavage 30 min prior to commencement of the stress. All animals were then housed in individual polycarbonate cages containing a clear 70×50 mm Pyrex crystallization dish inverted in the center. To begin the stress, water was added to each cage to within 0.5 cm of the top of the Pyrex dish. The fecal output of the animals was recorded at 30-min intervals for a 6-h period, during which they received no food or water. Stool output was expressed as the number of fecal pellets excreted over the 6-h collection period. Percent reduction was calculated by dividing the mean value from the treated animals (T) by the mean value from the control animals (C), subtracting the resulting quotient from 1.0, and multiplying by 100 [i.e., (1.0–T/C)×100].

EXAMPLE 4

Efficacy of CHX(3,4,3)-trans in Rats

CHX(3,4,3)-trans (1) was effective in the castor oil-induced diarrhea model. When administered sc at doses ranging from 0.0078 mg/kg to 24.9 mg/kg, there was a significant reduction in weight loss at all dose levels ($P<0.005$ to $P<0.001$, Table 1). In addition, the compound also significantly decreased stool output relative to controls at sc doses of 0.0156 mg/kg to 24.9 mg/kg, (P<0.001 for all doses, Table 1).

CHX(3,4,3)-trans was also remarkably effective at controlling IBS. When administered sc at doses ranging from 0.03 mg/kg to 0.99 mg/kg, there was a significant reduction in fecal output at all dose levels (P<0.001, Table 2). Oral administration of this compound also diminished fecal output at doses $\geq 5$ mg/kg (P$\leq$0.001, Table 2).

TABLE 1

Antidiarrheal Activity of Polyamine Analogues Predicated on a (3,4,3) Backbone[a]

| compd. no. | structure/abbreviation | dose per kg mg | dose per kg μmol | n | weight loss | P-value[c] | % reduction[d] |
|---|---|---|---|---|---|---|---|
| 1 | CHX(3,4,3)-trans | 0 | 0 | 20 | 11.6 ± 3.7 | — | — |
| | | 0.0078 | 0.0181 | 5 | 8.8 ± 1.2 | <0.005 | 24 |
| | | 0.0156 | 0.036 | 5 | 3.1 ± 1.2 | <0.001 | 73 |
| | | 0.03125 | 0.0726 | 5 | 4.2 ± 1.7 | <0.001 | 64 |
| | | 0.625 | 0.145 | 5 | 3.7 ± 0.8 | <0.001 | 68 |
| | | 0.125 | 0.29 | 5 | 4.1 ± 0.7 | <0.001 | 65 |
| | | 0.25 | 0.58 | 4 | 2.7 ± 0.7 | <0.001 | 77 |
| | | 0.5 | 1.16 | 5 | 2.9 ± 0.1 | <0.001 | 75 |
| | | 0.99 | 2.3 | 9 | 2.7 ± 1.3 | <0.001 | 77 |
| | | 4.97 | 11.6 | 5 | 1.6 ± 1.1 | <0.001 | 86 |
| | | 24.87 | 57.8 | 5 | 0.8 ± 0.7 | <0.001 | 93 |

| compd. no. | structure/abbreviation | stool output[e] | P-value[c] | % reduction[d] |
|---|---|---|---|---|
| 1 | CHX(3,4,3)-trans | 4.9 ± 2.0 | — | — |
| | | 3.6 ± 1.3 | >0.05 | NS |
| | | 0.4 ± 0.9 | <0.001 | 92 |
| | | 0 ± 0 | <0.001 | 100 |
| | | 0 ± 0 | <0.001 | 100 |
| | | 0 ± 0 | <0.001 | 100 |
| | | 0 ± 0 | <0.001 | 100 |
| | | 0 ± 0 | <0.001 | 100 |
| | | 0 ± 0 | <0.001 | 100 |
| | | 0 ± 0 | <0.001 | 100 |
| | | 0 ± 0 | <0.001 | 100 |

[a]Polyamine analogues were administered sc to rats at the doses shown in the table. Thirty minutes later, the rats were given castor oil, 5 mL/kg, by gavage. Stool output was monitored for 6 h after castor oil administration.
[b]Weight loss is expressed as g of weight lost per 350 g of rat weight over the 6-h experimental period.
[c]A one-tailed t-test assuming unequal variance was performed on the data of the treated vs control (0 mg/kg) animals for each compound. A value of P <0.05 was considered significant.
[d]Percent reduction was calculated by dividing the mean value from the treated animals (T) by the mean value from the control animals (C), subtracting the resulting quotient from 1.0, and multiplying by 100 [i.e., (1.0-T/C) × 100]. NS, not significant.
[e]Stool output is expressed as the g of stool excreted per 350 g of rat weight over the 6-h collection period. Data are not corrected for slight evaporative losses that occur during the assay. Such corrections do not significantly affect the results.

TABLE 2

Activity of Polyamine Analogues Against Stress-Induced Irritable Bowel Syndrome

| Structure/Abbreviation | Dose, kg$^{-1}$ mg | Dose, kg$^{-1}$ μmol | n | Stool Output[b] | P-Value | % Reduction[d] |
|---|---|---|---|---|---|---|
| CHX(3,4,3)-trans | 0 | 0 | 10 | 11.3 ± 4.1 | — | — |
| | 0.03125 | 0.0726 | 5 | 5.4 ± 2.1 | 0.001 | 52.2 |
| | 0.0625 | 0.145 | 5 | 2.2 ± 1.3 | <0.001 | 80.5 |
| | 0.125 | 0.29 | 5 | 0.6 ± 0.9 | <0.001 | 94.7 |
| | 0.25 | 0.58 | 5 | 0 ± 0 | <0.001 | 100 |

TABLE 2-continued

Activity of Polyamine Analogues Against Stress-Induced Irritable Bowel Syndrome

| Structure/Abbreviation | Dose, kg$^{-1}$ | | n | Stool Output[b] | P-Value | % Reduction[d] |
|---|---|---|---|---|---|---|
| | mg | μmol | | | | |
| | 0.5 | 1.16 | 5 | 0 ± 0 | <0.001 | 100 |
| | 0.99 | 2.3 | 5 | 0 ± 0 | <0.001 | 100 |

[a]Polyamine analogues were administered sc to rats at the doses shown in the table. Thirty minutes later, the rats were subjected to stress, i.e., a cage filled with water to within 1 cm of the height of a small dish. Stool output was monitored for 6 h after commencement of the stress.
[b]A cone-tailed t-test assuming unequal variance was performed on the data of the treated vs control (0 mg/kg) animals for each compound. A value of P <0.05 was considered significant.
[c]Stool output is expressed as the number of fecal pellets excreted over the 6-h collection period.
[d]Percent reduction was calculated by dividing the mean value from the treated animals (T) by the mean value from the control animals (C), subtracting the resulting quotient from 1.0, and multiplying by 100 [i.e., (1.0-T/C) × 100]. NS, not significant.

What is claimed is:

1. A method of treating diarrhea or gastrointestinal spasm in a human or non-human animal in need thereof comprising administering to said animal an effective amount of a compound having the formula:

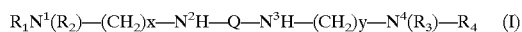

$$R_1N^1(R_2)\text{—}(CH_2)x\text{—}N^2H\text{—}Q\text{—}N^3H\text{—}(CH_2)y\text{—}N^4(R_3)\text{—}R_4 \quad (I)$$

wherein: $R_1$, $R_2$, $R_3$ and $R_4$ are the same or different and are H, alkyl, cycloalkyl or aralkyl having from 1 to 12 carbon atoms, or $R_1$ and $R_2$ and/or $R_3$ and $R_4$ form a heterocyclic group having from 3 to 10 atoms wherein the hetero atom is said $N^1$ or $N^4$;

Q is a cycloalkyl group having from 3 to 10 carbon atoms;

x is an integer from 3 to 6, inclusive;

and y is an integer from 3 to 6, inclusive;

or (II) a salt thereof with a pharmaceutically acceptable acid.

2. The method according to claim 1 wherein Q is connected either cis or trans as the (1,2), (1,3), (1,4), (1,5) or (1,6) isomer.

3. The method according to claim 1 wherein Q is cyclohexyl.

4. The method according to claim 1 wherein x is 3 and y is 3.

5. The method according to claim 1 wherein x is 3, y is 3, $R_1$ and $R_3$ are both H and $R_2$ and $R_4$ are both ethyl.

6. The method according to claim 1 wherein Q is cyclohexyl; x and y are 3; $R_1$ and $R_3$ are both H, and $R_2$ and $R_4$ are both ethyl.

7. The method according to claim 6 wherein said polyamine is the trans (1,4) isomer.

* * * * *